US011510961B2

(12) United States Patent
Ruff (10) Patent No.: US 11,510,961 B2
(45) Date of Patent: Nov. 29, 2022

(54) METHODS AND COMPOSITIONS FOR USE OF A CHEMOKINE RECEPTOR ANTAGONIST PEPTIDE TO TREAT ADDICTION, SUBSTANCE ABUSE DISORDERS OR SYMPTOMS THEREOF

(71) Applicant: Creative Bio-Peptides Inc., Potomac, MD (US)

(72) Inventor: Michael R. Ruff, Potomac, MD (US)

(73) Assignee: Creative Bio-Peptides, Inc., Potomac, MD (US)

( * ) Notice: Subject to any disclaimer, the term of this patent is extended or adjusted under 35 U.S.C. 154(b) by 0 days.

(21) Appl. No.: 17/129,837

(22) Filed: Dec. 21, 2020

(65) Prior Publication Data
US 2021/0187057 A1 Jun. 24, 2021

Related U.S. Application Data

(60) Provisional application No. 62/950,776, filed on Dec. 19, 2019.

(51) Int. Cl.
| | | |
|---|---|---|
| A61K 38/08 | (2019.01) | |
| A61P 25/30 | (2006.01) | |
| A61P 25/36 | (2006.01) | |
| A61P 25/04 | (2006.01) | |
| C07K 7/06 | (2006.01) | |

(52) U.S. Cl.
CPC .............. *A61K 38/08* (2013.01); *A61P 25/30* (2018.01); *A61P 25/36* (2018.01)

(58) Field of Classification Search
CPC .......... A61K 38/08; A61P 25/30; A61P 25/36; A61P 25/04; C07K 7/06
See application file for complete search history.

(56) References Cited

U.S. PATENT DOCUMENTS

| | | | |
|---|---|---|---|
| 5,063,206 A | 11/1991 | Bridge | |
| 5,276,016 A | 1/1994 | Pert | |
| 5,514,670 A | 5/1996 | Friedman | |
| 5,529,983 A | 6/1996 | Pert | |
| 5,534,495 A | 7/1996 | Pert | |
| 5,739,109 A | 4/1998 | Galpin | |
| 5,756,449 A | 5/1998 | Andersen | |
| 5,834,429 A | 11/1998 | Pert | |
| 5,863,718 A | 1/1999 | Pert | |
| 6,011,014 A | 1/2000 | Andersen | |
| 6,242,564 B1 | 6/2001 | Pert | |
| 6,265,374 B1 | 7/2001 | Andersen | |
| 7,390,788 B2 | 6/2008 | Pert | |
| 7,700,115 B2 | 4/2010 | Ruff | |
| 8,916,517 B2 | 12/2014 | Coy | |
| 10,130,674 B2 | 11/2018 | Pert | |
| 2005/0013809 A1* | 1/2005 | Owens | C07K 16/44 424/130.1 |
| 2011/0178013 A1 | 7/2011 | Paternostre | |
| 2011/0245180 A1 | 10/2011 | Pert | |
| 2014/0322251 A1 | 10/2014 | Ruff | |
| 2014/0322252 A1 | 10/2014 | Ruff | |
| 2014/0323393 A1 | 10/2014 | Ruff | |
| 2018/0344798 A1 | 12/2018 | Ruff | |
| 2018/0360907 A1 | 12/2018 | Ruff | |
| 2019/0022166 A1 | 1/2019 | Ruff | |
| 2019/0125823 A1* | 5/2019 | Ruff | A61P 25/04 |

FOREIGN PATENT DOCUMENTS

| | | | | |
|---|---|---|---|---|
| JP | 11512732 A | 11/1999 | | |
| WO | WO-2010084851 A1 * | 7/2010 | | A61P 29/00 |

OTHER PUBLICATIONS

Mahalakshmi et al., "The Use of D-Amino Acids in Peptide Design," A New Frontier in Amino Acid and Protein Research, 2006, Chapter 5.9, pp. 415-430. (Year: 2006).*
"Amphetamines" from www.DEA.gov, pp. 1-4. Accessed Oct. 26, 2021. (Year: 2021).*
Abboud, et al., Inflammation Following Traumatic Brain Injury in Humans: Insights from Data-Driven and Mechanistic Models into Survival and Death. Front Pharmacol, 2016, vol. 7, 342.
Altman et al., Failure of vaccine test is setback in AIDS fight. New York Times, Sep. 22, 2007, 2 pages.
Arisi, et al., Increased CCL2, CCL3, CCL5, and IL-1β cytokine concentration in piriform cortex, hippocampus, and heocortex after pilocarpine-induced seizures. J Neuroinflammation, 2015, vol. 12, 129, p. 1-7.
Bamburg, et al., Actin dynamics and cofilin-actin rods in Alzheimer disease, Cytoskeleton, 2016, vol. 73, No. 9, p. 477-497.
Bamburg, et al., ADF/cofilin-actin rods in neurodegenerative diseases, Curr Alzheimer Res., 2010, vol. 7, No. 3, p. 241-250.
Barrett, et al., NOX2 deficiency alters macrophage phenotype through an IL-10/STAT3 dependent mechanism: implications for traumatic brain injury. J Neuroinflammation, 2017, vol. 14(65), p. 1-17.
Brenneman et al., Peptide T sequences prevent neuronal cell death produced by the envelope protein (gp120) of the human immunodeficiency virus. Drug Devel Res, 1988, vol. 15, p. 361-369.
Cai et al., Two different molecular mechanisms underlying progesterone neuroprotection against ischemic brain Damage. Neuropharmacology, 2008, vol. 55, p. 127-38.

(Continued)

*Primary Examiner* — Julie Ha
(74) *Attorney, Agent, or Firm* — Greenberg Traurig, LLP (57) ABSTRACT

A method of treating a person with a substance abuse disorder, in particular, opioid abuse and psychostimulant abuse with a chemokine receptor antagonist pharmaceutical composition. The antagonist comprising five contiguous amino acids having the general structure: A-B-C-D-E in which A is Ser, Thr, Asn, Glu, or Ile; B is Ser, Thr, Asp, or Asn; C is Thr, Ser, Asn, Arg, or Trp; D is Tyr and E is Thr, Ser, Arg, or Gly. The amino acids are D stereoisomers. The method both relieves a person's symptoms and reduces the person's risks of addiction.

8 Claims, 8 Drawing Sheets
Specification includes a Sequence Listing.

(56) References Cited

OTHER PUBLICATIONS

Cerri, et al., The Chemokine CCL2 Mediates the Seizure-enhancing Effects of Systemic Inflammation. J Neurosci, 2016, vol. 36, p. 3777-3788.

Chen C, Zhang XR, Ju ZY, He WF., Advances in the research of cytokine storm mechanism induced by Corona Virus Disease 2019 and the corresponding immunotherapies, Chinese Journal of Burns. 2020; vol. 36(06), p. 471-475, E005, Epub Mar. 3, 2020.

Chen Y, Guo Y, Pan Y, Zhao ZJ. Structure analysis of the receptor binding of 2019-nCo V. Biochem Biophys Res Commun. 2020. Epub Feb. 23, 2020.

Cichon et al., Cofilin Aggregation Blocks Intracellular Trafficking and Induces Synaptic Loss in Hippocampal Neurons, Journal of Biological Chemistry, vol. 287, No. 6, p. 3919-2929, 2012.

Crews et al. Induction of innate immune genes in brain create the neurobiology of addiction. Brain, Behavior, and Immunity, 2011, vol. 25, Suppl 1, S4-S12. Epub Mar. 16, 2011.

Dhote et al., Prolonged inflammatory gene response following soman-induced seizures in mice. Toxicology, 2007, vol. 238, p. 166-176.

Di Prisco, et al., Functional adaptation of presynaptic chemokine receptors in EAE mouse central nervous system. Synapse, 2014, vol. 68, p. 529-535.

Di Prisco, et al., RANTES-mediated control of excitatory amino acid release in mouse spinal cord. J Neurochem, 2012, vol. 121, p. 428-437.

Dillman, et al., Gene expression profiling of rat hippocampus following exposure to the acetylcholinesterase inhibitor soman. Chem Res Toxicol 2009, vol. 22, p. 633-638.

Ensign, et al., Nanoparticle-based drug delivery to the vagina: A review. J Control Release, 2014, p. 500-514.

Fan, Y et al., MKEY, a Peptide Inhibitor of CXCL4-CCL5 Heterodimer Formation, Protects Against Stroke in Mice. Journal of the American Heart Association. Sep. 15, 2016, vol. 5, No. 9; pp. 1-8.

Feng, Z et al., Inspiration from the mirror: D-amino acid containing peptides in biomedical approaches. Biomolecular Concepts Jun. 1, 2016, vol. 7, No. 3; pp. 179-187.

Flannery, et al., Persistent neuroinflammation and cognitive impairment in a rat model of acute diisopropylfluorophosphate intoxication. J Neuroinflammation 2016, vol. 13, No. 267, p. 1-16.

Funke, SA et al., Peptides for Therapy and Diagnosis of Alzheimer's Disease. Current Pharmaceutical Design. 2012, vol. 18, No. 6; pp. 755-767.

Gibson et al., Feasibility of progesterone treatment for ischaemic stroke. J. Cerebral Blood Flow & Metabolism, 2016, vol. 36(3), p. 487-91.

Goodwin et al., "Peptides as therapeutics with enhanced bioactivity" Current Medicinal Chemistry 2012, vol. 19, p. 4451-4461.

Hayball, P. J. 1996. Chirality and nonsteroidal anti-inflammatory drugs. Drugs vol. 52 Suppl 5: p. 47-58.

He et al., Increased MCP-1 and microglia in various regions of the human alcoholic brain. Experimental Neurology, 2008, vol. 210(2), p. 349-58. Epub Jan. 15, 2008.

Heijo et al., Interactions Between Peptide and Preservatives: Effects on Peptide Self-Interactions and Antimicrobial Efficiency in Aqueous Multi-Dose Formulations, Pharm Res, 2015, vol. 32, p. 3201-3212.

Heseltine, et al., Randomized double-blind placebo-controlled trial of peptide T for HIV-associated cognitive impairment. Arch Neurol, 1998, vol. 55, p. 41-51.

Hill et al., HIV envelope protein-induced neuronal damage and retardation of behavioral development in rat neonates. Brain Res, 1993, vol. 603(2), p. 222-33.

Huang et al., Clinical features of patients infected with 2019 novel coronavirus in Wuhan, China. Lancet. 2020, vol. 395, No. 10223, p. 497-506. Epub Jan. 28, 2020.

International Search Report for PCT/US19/40977 dated Jan. 13, 2020.

Joy et al., CCR5 Is a Therapeutic Target for Recovery after Stroke and Traumatic Brain Injury. Cell, 2019, vol. 176(5), p. 1143-57 e13. Epub Feb. 23, 2019.

Kang et al., Cofilin, a Master Node Regulating Cytoskeletal Pathogenesis in Alzheimer's Disease, Journal of Alzheimer's Disease, 2019, vol. 72, S131-S144.

Kim et al., Chemokines and cocaine: CXCR4 receptor antagonist AMD3100 attenuates cocaine place preference and locomotor stimulation in rats. Brain, Behavior, and Immunity, 2017, vol. 62, p. 30-4. Epub Aug. 31, 2016.

Lee et al., Decreased pain responses of C-C chemokine receptor 5 knockout mice to chemical or inflammatory stimuli. Neuropharmacology, 2013, vol. 67, p. 57-65.

Li, et al., Effects of CC-chemokine receptor 5 on ROCK2 and P-MLC2 expression after focal cerebral ischaemia-reperfusion injury in rats. Brain Inj, 2016, vol. 30, p. 468-473.

Louboutin, et al., Role of CCR5 and its ligands in the control of vascular inflammation and leukocyte recruitment required for acute excitotoxic seizure induction and neural damage. FASEB J, 2011, vol. 25, p. 737-753.

Lusso et al., Cryptic Nature of a Conserved, CD4-Inducible V3 Loop Neutralization Epitope in the Native Envelope Glycoprotein Oligomer of CCR5-Restricted, but Not CXCR4-Using, Primary Human Immunodeficiency Virus Type 1 Strains. J Virol. 2005, vol. 79(11), p. 6957-68.

Mao, et al., Exogenous administration of PACAP alleviates traumatic brain injury in rats through a mechanism involving the TLR4/MyD88/NF-κB pathway. J Neurotrauma, 2012, vol. 29, p. 1941-1959.

Marastoni et al. Synthesis, metabolic stability and chemotactic activity of peptide T and its analogues. J Peptide Protein Res. 1990. vol. 35, p. 81-88.

Mayo Clinic (https://www.mayoclinic.org/diseases-conditions/traumatic-brain-injury/diagnosis-treatment/drc-20378561, 2019.

Mehta et al., Across Speciality Collaboration UK. COVID-19: consider cytokine storm syndromes and immunosuppression. Lancet. 2020. Epub Mar. 13, 2020.

Melgarejo, et al., Monocyte chemoattractant protein-I: a key mediator in inflammatory processes. The International Journal of Biochemistry & Cell Biology. 2009; vol. 41(5): p. 998-1001. Epub Sep. 2, 2008.

Merck Manual (<https://www.merckmanuals.com/professional/neurologic-disorders/peripheral-nervous-system-and-motor-unit-disorders/amyotrophic-lateral-sclerosis-als-and-other-motor-neuron-diseases-mnds> accessed on Sep. 17, 2021).

Moore et al. In vivo depression of lymphocyte traffic in sheep by VIP and HIV (AIDS)-related peptides. Immunopharmacology, 1988, vol. 16, p. 181-89.

Morganti, et al., Age exacerbates the CCR2/5-mediated neuroinflammatory response to traumatic brain injury. J Neuroinflammation 2016, vol. 13, p. 1-12.

Nayak et al., Chemokine CCR5 and cocaine interactions in the brain: Cocaine enhances mesolimbic CCR5 mRNA levels and produces place preference and locomotor activation that are reduced by a CCR5 antagonist. Brain, Behavior, and Immunity, 2020, vol. 83, 288-92. Epub Sep. 27, 2019.

NIH (<https://www.ninds.nih.gov/Disorders/All-Disorders/Encephalopathy-Information-Page> accessed Aug. 3, 2018).

Owen et al., A theta-defensin composed exclusively of D-amino acids is active against H I V-1. J. Peptide Res, 2004, vol. 53, p. 469-76.

Padi et al., Attenuation of rodent neuropathic pain by an orally active peptide, RAP-103, which potently blocks CCR2-and CCR5-mediated monocyte chemotaxis and inflammation. Pain, 2012, vol. 153(1), p. 95-106. PubMed PMID: 22033364.

Paoletti, et al., Amygdalin analogues inhibit IFN-gamma signalling and reduce the inflammatory response in human epidermal keratinocytes. Inflammation, 2013, vol. 36, p. 1316-1326.

Peiris JS, Guan Y, Yuen KY. Severe acute respiratory syndrome. Nat Med. 2004; vol. 10(12 Suppl), S88-97. Epub Dec. 4, 2004.

Pert et al., Octapeptides deduced from the neuropeptide receptor-like pattern of antigen T 4 in brain potently inhibit human immunodeficiency virus receptor binding and T-cell infectivity. Proc Natl Acad Sci USA, 1986, vol. 83, p. 9254-9258.

(56) References Cited

OTHER PUBLICATIONS

Polito, et al., Epithelia cells as regulators of airway inflammation. The Journal of Allergy and Clinical Immunology. 1998, vol. 102(5), p. 714-8. Epub Dec. 29, 1998.

Rachaudhuri S. P., E. M. Farber, and S. K. Raychaudhuri. 1999. Immunomodulatory effects of peptide T on Th 1/Th 2 cytokines. Int J Immunopharmacol, 1999, vol. 21, p. 609-15.

Ravizza, et al., Innate and adaptive immunity during epileptogenesis and spontaneous seizures: evidence from experimental models and human temporal lobe epilepsy. Neurobiol Dis, 2008, vol. 29, p. 142-160.

Rosi et al. Chemokine receptor 5 antagonist d-ALA-peptide T-amide reduces microglia and astrocyte activation within the hippocampus in a neuroinflammatory rat model of alzheimer's disease. Neuroscience, 2005, vol. 134, p. 671-676.

Ruan et al., Clinical predictors of mortality due to COVID-19 based on an analysis of data of 150 patients from Wuhan, China. Intensive Care Medicine. 2020. Epub Mar. 4, 2020.

Ruff et al., CD4 receptor binding peptides that block HIV infectivity cause human monocyte chemotaxis. Relationship a vasoactive intestinal polypeptide. FEBS Lett, 1987, vol. 211, p. 17-22.

Ruff et al., Peptide T[4-8] is Core HIV Envelope Sequence Required for CD4 Receptor Attachment, Lancet. 1987. vol. 330(8561), p. 751.

Ruff et al., Update on D-ala-peptide T-amide (DAPTA): a viral entry inhibitor that blocks CCR5 chemokine receptors. Curr HIV Res, 2003, vol. 1, p. 51-67.

Saez-Torres et al., Peptide T does not ameliorate experimental autoimmune encephalomyelitis (EAE) in Lewis rats, Clin. Exp. Lmmunol, 2000, vol. 121, p. 151-56.

Saika et al., CC-chemokine ligand 4/macrophage inflammatory protein-1beta participates in the induction of neuropathic pain after peripheral nerve injury. Eur J Pain, 2012, vol. 16, p. 1271-1280.

Saika et al., Chemokine CXCL1 is responsible for cocaine-induced reward in mice. Neuropsychopharmacology Reports. 2018, vol. 38(3), p. 145-8. Epub Sep. 4, 2018.

Servick, Unexpected drug emerges for stroke recovery. Science. Feb. 22, 2019. vol. 363(6429), p. 805.

Shen et al., . Postnatal activation of TLR4 in astrocytes promotes excitatory synaptogenesis in hippocampal neurons. J Cell Biol, 2016, vol. 215, p. 719-734.

Shi et al., COVID-19 infection: the perspectives on immune responses. Cell Death Differ. 2020. Epub Mar. 25, 2020.

Smith et al., Tritiated D-ala-peptide T binding: A pharmacologic basis for the design of drugs which inhibit HIV receptor binding. Drug Development Res, 1988, vol. 15, p. 371-379.

Song et al., "Effects of an Inhibitor of Monocyte Recruitment on Recovery from Traumatic Brain Injury in Mice Treated with Granulocyte Colony-Stimulating Factor," Int. J. Mol. Sci. Jul. 2, 2017; vol. 18(7), p. 1-16.

Song et al., Pharmacological Modulation of Functional Phenotypes of Microglia in Neurodegenerative Diseases. Front Aging Neurosci, 2017, vol. 9, p. 1-10.

Spisani et al. Chemotactic response of human monocytes to pentapeptide analog derived from immunodeficiency virus protein gp 120. Inflammation, 1990, vol. 14(1), p. 55-60.

Stern et al. Drug Delivery: Oral Delivery of Peptides by Petelligence Technology. Drug Development and Delivery. Accessed online at https://drug-dev.com/oral-delivery-of-peptides-by-peptelligence-technology on Aug. 5, 2019, 10 pages. (Year: 2013).

The Concussion Legacy Foundation (https://concussionfoundation.org/CTE-resources/what-is-CTE, 2019).

THERMO, N-Terminal Acetylation and C-Terminal Amidation of Peptides. Technical Information, 2004, 2 pages.

Trocello et al., Implication of CCR2 chemokine receptor in cocaine-induced sensitization. J Mol Neurosci. 2011, vol. 44(3), p. 147-51. Epub Mar. 23, 2011.

Valekova et al., Revelation of the IFN$\alpha$, IL-10, IL-8 and IL-1$\beta$ as promising biomarkers reflecting immuno-pathological mechanisms in porcine Huntington's disease model. J Neuroimmunol, 2016 vol. 293, p. 71-81.

Vezzani et al., Brain inflammation as a biomarker in epilepsy. Biomark Med, 2011, vol. 5, p. 607-614.

Vezzani et al., The role of inflammation in epilepsy. Nat Rev Neurol, 2011, vol. 7, p. 31-40.

Victoria, et al. Knockdown of C-C chemokine receptor 5 (CCR5) is protective against cerebral ischemia and reperfusion injury. Curr Neurovasc Res, 2017.

Villemagne et al., Peptide T and glucose metabolism in AIDS dementia complex. J Nucl Med, 1996, vol. 37, 1177-1180.

Vitaliti et al., Targeting inflammation as a therapeutic strategy for drug-resistant epilepsies: an update of new immune-modulating approaches. Hum Vaccin Immunother, 2014, vol. 10, 868-875.

Walsh et al., Amyloid-$\beta$ and Proinflammatory Cytokines Utilize a Prion Protein-Dependent Pathway to Activate NADPH Oxidase and Induce Cofilin-Actin Rods in Hippocampal Neurons, PLOS One, 2014, vol. 9, Issue 4, e95995, p. 1-12.

Xu et al., Pathological findings of COVID-19 associated with acute respiratory distress syndrome. Lancet Respir Med. 2020. Epub Feb. 23, 2020.

Yoshikawa et al., Severe acute respiratory syndrome (SARS) coronavirus-induced lung epithelial cytokines exacerbate SARS pathogenesis by modulating intrinsic functions of monocyte-derived macrophages and dendritic cells. J Virol. 8 2009, vol. 83(7), p. 3039-48. Epub Nov. 14, 2008.

Yousefzadeh-Chabok et al., "The Relationship Between Serum Levels of Interleukins 6, 8, 10 and Clinical Outcome in Patients with Severe Traumatic Brain Injury." Arch Trauma Res, 2015, vol. 4(1), p. e18357.

Zhao, Q., Dual targeting of CCR2 and CCR5: therapeutic potential for immunologic and cardiovascular diseases. J Leukoc Biol, 2010, vol. 88, Issue 1, p. 41-55.

Zhou et al., CCR5 is a suppressor for cortical plasticity and hippocampal learning and memory. Elife. 2016;5. Epub Dec. 21, 2016.

\* cited by examiner

METHODS AND COMPOSITIONS FOR USE OF A CHEMOKINE RECEPTOR ANTAGONIST PEPTIDE TO TREAT ADDICTION, SUBSTANCE ABUSE DISORDERS OR SYMPTOMS THEREOF

STATEMENT AS TO FEDERALLY SPONSORED RESEARCH

This invention was made with government support under Contract numbers R01 DA045499 and P30 DA013429 awarded by the U.S. Department of Health & Human Services. The government has certain rights in the invention.

In 2019 there were >20 million SUDs and >8.3 million illicit drug use disorder cases in the US with 50,042 deaths involving opioids. Psychostimulants cocaine and methamphetamine accounted for >2 million SUDs, which often results in death from overdose, especially when combined with an opioid. Almost 74% of adults suffering from a substance use disorder also struggled with an alcohol use disorder. Drug abuse and addiction cost American society more than $740 billion annually in lost workplace productivity, healthcare expenses, and crime-related costs.

Although new examples are constantly emerging, common drugs of abuse or substances of abuse include nicotine, opioids, cocaine, methamphetamine, benzodiazepines, central nervous system depressants, ketamine, cathinones, PCP, *cannabis*, hallucinogens, alcohol, MDMA, and Gamma-hydroxybutyrate, which in many cases have a dependence or addiction liability which is now understood to be a result of persistent, progressive neuroinflammation. This neuroinflammation involves activation of the innate immune system in the brain which is stimulated by drugs of abuse and substance abuse in general. Thus, it is becoming increasingly clear that neuroinflammation is a significant contributor to many neuropsychiatric disorders (e.g., opioid use disorders, cocaine addiction, depression and anxiety). The chemokine receptor antagonist (CRA) drug family is effective in blocking neuroinflammation and thus can be a treatment to mitigate dependence or addiction liabilities for drugs that may be abused.

Traditionally, addiction from opioids or psychostimulants was viewed as a solely neuronal process. However new evidence now shows the importance of innate immune system activation in opioid and psychostimulant pharmacology, drug-seeking behaviors, and addiction. This neuro-immune process involves cytokines, chemokines, and toll-receptors (TLR4), all of which can be blocked by the peptides of the invention.

Regardless of the route of administration, or even the specific drug used, psychostimulants produce the same basic spectrum of acute CNS effects: euphoria, increased energy/decreased fatigue, reduced need for sleep, decreased appetite, decreased distractibility, increased self-confidence and alertness, increased libido, and prolonged orgasm. Peripheral effects may include tremor, diaphoresis, increased muscle tension, tachypnea, hyperreflexia, and hyperpyrexia. Over several hours, days, or weeks, psychostimulant use can result in restlessness, irritability, and insomnia and at higher doses, suspiciousness, repetitive stereotyped behaviors, and bruxism.

Withdrawal from psychostimulants often includes hypersomnia, increased appetite, and depressed mood. Acute withdrawal typically lasts 7-10 days, but residual symptoms, possibly associated with neurotoxicity, may persist for several months. Behavioral therapies, including Cognitive-Behavioral Therapy (CBT), the Community Reinforcement Approach (CRA), contingency management, combinations of these, and others remain the mainstay of treatment for stimulant-use disorders with only modest benefits. Unlike as for opioids, no pharmacologic treatments exist for psychostimulant addiction. The peptides of the invention can mitigate and treat opioid and psychostimulant CNS effects and withdrawal to provide for these unmet medical needs.

A new approach is to treat addictions and substance abuse is via the innate immune system cytokines, chemokines and their receptors (1, 2) which are now recognized as having controlling roles in the brain, in addition to classical neurotransmitters and neuropeptides. The purpose of the brain's innate immune system is to protect the brain from injury, damage, stress, infections, and to promote repair, regeneration, and neurogenesis. However, in the presence of drugs of abuse and alcohol, the innate immune system becomes pathologically activated so that the microglia and astrocytes in the addiction-controlling (reward) brain areas progress to an inflammatory state. All addictive drugs activate NF-κB, the key transcription factor involved in induction of innate immune genes in microglia monocytes, and astrocytes. NF-κB controls the transcription of many inflammatory genes particularly chemokines, cytokines, oxidases and proteases, whose activation occurs concomitantly with the development of addiction. Once activated these cells and their secreted inflammatory mediators desensitize opioid receptors, block neurogenesis, destroy synapses, kill neurons, alter cognition and promote risk and drug seeking behaviors. Therefore, the molecular causes of substance abuse and addiction can better be treated at the level of its constituent innate immune receptors and biomolecules.

Opioids, psycho-stimulants, including cocaine, methamphetamine and designer cathinones and other psychostimulants, as well as pharmaceutical treatments for attention deficit/hyperactivity disorder (ADHD) that contain amphetamine-based stimulants Adderall (amphetamine and dextroamphetamine salts), methamphetamine hydrochloride (Desoxyn), dextroamphetamine sulfate (Dexedrine), dextromethamphetamine (Dextrostat), dextromethylphenidate (Focalin), methylphenidate (Concerta, Daytrana, Metadate, Methyln, Ritalin), cannabinoids and other substances that promote dependence or addiction liability share commonalities, including dysregulated dopamine (DA) systems that facilitate reward, reinforcement and relapse. Behavioral findings, primarily with psycho-stimulants so far, show that a CXCR4 antagonist (AMD3100) inhibits cocaine reward and locomotor activation (3) and cocaine taking in rat self-administration assays that model human drug taking. The mesolimbic chemokine CCR5 receptor system also appears positioned to influence cocaine reward as CCR5 knockout mice display fewer dopamine neurons, lower striatal dopamine levels, and reduced locomotor activation compared to wild types. Additional behavioral data indicate that the CCR5 antagonist Maraviroc, an approved CCR5 antagonist, reduces rewarding and locomotor-activating effects of cocaine (4). An antagonist of CCR2 (INCB 3284) prevented psychostimulant-induced CPP and CCR2 genetic knockdown reduces sensitization to the locomotor-activating effects of cocaine (5), identifying CCR2 as a further therapeutic target in reward pathways.

At the cellular level, cocaine exposure increases mRNA levels of CXCL12 in the midbrain ventral tegmental area (VTA), CCR5 (3-fold increase) in the nucleus accumbens and CCL2 in the prefrontal cortex (6). Our interpretation is that drugs of abuse increase levels of chemokine ligands (e.g. CXCL12, CCL5, CCL2) in input regions like ventral tegmental area (VTA) of the mesolimbic system, leading to enhanced DA transmission that drives increased drug seeking and taking.

Plasma levels of the chemokine CXCL12 are elevated in mice following acute cocaine exposure and decreased in human cocaine abusers during withdrawal. Repeated cocaine exposure produced a significant increase in CXCL12 mRNA expression in the VTA suggesting that the CXCL12/CXCR4 system in the brain reward circuit is impacted by cocaine exposure and influences behavioral effects related to the abuse liability of cocaine.

CXCL12 is a chemokine identified in the brain which can modulate dopamine transmission through activation of its receptor CXCR4. The CXCR4 antagonist AMD 3100 (Plerixafor) inhibits conditioned place preference (CPP) and locomotor activation produced by cocaine. In addition, AMD 3100 (5, 10 mg/kg) pretreatment reduced locomotor activation produced by an acute cocaine injection but did not affect basal locomotor activity relative to saline-injected controls. Those results suggest that the CXCL12/CXCR4 system in the brain reward circuit is impacted by cocaine exposure and antagonists can inhibit behavioral effects related to the abuse liability of cocaine (3).

The CRA small peptide R103, an antagonist of multiple (CCR2/5/8, CXCR4) chemokine receptors involved in brain inflammation that promotes substance abuse disorders, will block the cascade of neuroinflammation and thus will prevent the creation of a dopamine/cytokine dependent heightened rewarding response that is the basis of the stimulating/rewarding effects of cocaine and other drugs of abuse that produce addiction. Blocking the cascade of chemokine induced effects with R103 is predicted to reduce symptoms of withdrawal upon drug dose reduction or cessation and is a further aspect of addiction treatment by these compounds.

The chemokine system provides a neuroimmune-based therapeutic avenue that can counteract opioid use disorder and other substance abuse disorders by reducing DA transmission. Given that CCR5, CCR2, CCR8 and CXCR4 receptors influence neurochemical metrics of drug addiction, the multi-chemokine antagonist small peptide R103 may have superior abilities to reduce drug induced behaviors, including drug-seeking and dependence elicited by common drugs of abuse (some examples are opioids, cocaine, psychostimulants, and alcohol). Blocking the activity of chemokines via the administration of the peptides of the invention can minimize undesirable and adverse drug effects, the risk of addiction and substance abuse. Chemokine receptor antagonists (CRA) can further be useful in mitigating drug-seeking behaviors by reversing opioid tolerance and normalizing dysfunctional chemokine-associated reward pathways in OUD.

Neuroinflammation in the dorsal anterior cingulate cortex (dACC) produces arousal and behavioral changes that indicate social anxiety in humans. Therefore, the peptides of the invention could be used to treat social anxiety and related disorders. In other models and human clinical studies, there is evidence that neuroinflammation can also lead to depression, therefore these peptides would be useful in treating depression which is strongly associated with substance abuse and seems to be part of the same chemokine mediated processes.

Blocking Chemokine Receptor Activation by Several of the Multi-Chemokine Antagonist Peptides of this Invention.

Table 1 illustrates the potencies of several peptides of the invention to inhibit chemokine receptors CCR2/CCR5. These receptor-active peptides (Receptides, abbreviated as RAP's) represent a novel, safe and non-addictive pharmacological intervention for substance abuse disorders by normalizing the neurobiology of addiction to suppress drug-seeking behaviors, reduce psychostimulant (cocaine, methamphetamine) activation and locomotion, and inhibit consumption of alcohol, other drugs of abuse and substance abuse in general. They may also treat depression and anxiety as those commonly occur in substance abuse. Targeting chemokine receptors with RAP-103 and related small all-D-pentapeptides to block chemokine receptors that incite drug abuse (1, 2) will reduce addiction behaviors (drug-seeking) and withdrawal symptoms to protect against relapse of drug-taking behaviors to reduce substance abuse in general to become superior treatments for substance abuse disorders. Decades-old treatments (methadone, buprenorphine etc.) require extended use, suffer from high recidivism, are only partly effective and are clearly inadequate. New treatments with no abuse liability, that blunt drug-seeking, dependence, and facilitate recovery and withdrawal are a priority need.

TABLE 1

| Peptide D amino acid sequences | | Potency EC50 pM |
|---|---|---|
| SEQ ID No.: 1 | TTNYT (RAP-103) | 10 |
| SEQ ID No.: 2 | SSTYR | 1 |
| SEQ ID No.: 3 | STNYT | 3 |
| SEQ ID No.: 4 | NTSYG | 10 |
| SEQ ID No.: 5 | dASTTNYT-NH$_2$ (Dala$_1$-peptide T-amide) | 10 |
| SEQ ID No.: 6 | ASTTNYT (RAP-310) | 10 |

METHODS

Because opioids are used in the management of pain conditions that contribute to OUD, we determined the efficacy of a small peptide chemokine receptor antagonist RAP-103 (all-D-TTNYT, SEQ ID #1, Table 1), sometimes called RAP-103 or R103) to reverse opioid receptor analgesic tolerance and block pain as a test of its ability to block-drug seeking behaviors. Painful diabetic neuropathy (PDN) is a common complication of diabetes which adversely affects patients' daily life, often involves opioid use, which creates an addiction risk. We reasoned that chronic inflammation blocked by R103 that causes chronic pain is also engaged in the pathogenesis of OUD and substance abuse, then a demonstration of 1) blocking infiltration of immune cells in damaged nerves and/or activation of spinal microglia in the development of pain; and 2) inhibiting inflammatory responses in the peripheral and/or the central nervous system that reduces chronic pain would also reduce chronic inflammation in the brain that leads to substance abuse behaviors. To test the hypothesis, we first used behavioral and molecular/cellular approaches to explore chronic pain development and inflammatory reaction in Streptozotocin (STZ) induced diabetic rats. Our results showed that following the induction of diabetes, rats exhibited persistent mechanical and cold allodynia (up to five months post-induction). The levels of inflammatory molecules, including cytokines, IL1b and TNFa; chemokines CCL2, CCL3; and chemokines receptors CCR2 and CCR5 were dramatically increased in sciatic nerves. Microglia in the spinal cord dorsal horns became activated with hypertrophic morphology and an increase in microglial cell number. CCL2 and CCL3 are two chemokines well known in mediating immune cell trafficking and immune response in the context of neuropathic pain. Oral administration of RAP-103 a CCR2/CCR5/CCR8 multi-CRA receptor antagonist for 7 days inhibited expression of chemokines and cytokines and reduced neuropathic pain. Thus R103 has the predicted treatment effect to blunt drug-seeking behaviors or psychostimulant activation (e.g. locomotion).

The treatment with R103 (RAP-103) (0.5-0.02 mg/Kg b.w., daily, for 7 days, resulted in a complete reversal of established hypersensitivity in STZ rats. The results suggest that functional antagonism of multiple chemokine receptors and innate immune receptors may be treatments and medicines for pain and inflammation. In view of the results showing that chemokines reduce opioid efficacy by cross-desensitizing opioid receptors, these results suggest that administration of a chemokine receptor antagonist peptides of the invention, will reduce addiction risk, and in those suffering from drug addiction, provide a treatment to block or reduce drug-seeking behaviors and limit the symptoms of withdrawal. The effective human doses suggested by these animal studies would be 0.01 to 20 mg/Kg/day. The peptides may be dosed as an oral pill, suspension, liquid, or by IV and subcutaneous injections to achieve pain control with decreased concomitant opioid use. Some examples of other useful CRA antagonists that can reduce drug-seeking/substance abuse are Maraviroc (a CCR5 antagonist) or AMD3100 (a CXCR4 antagonist). The peptides of the current invention have the advantage of blocking multiple chemokine receptors (CCR2, CCR5, CCR8, CXCR4) and pathways (NFkB, STAT3, TLR4) involved in substance abuse and are safer.

Induction and Assessment of Diabetes in Rats

Rats were fasted overnight and received a single intraperitoneal injection of streptozotocin (60 mg/kg, Sigma-Aldrich) in citrate buffer (pH 4.5) to induce type I diabetes. The induction of diabetes was confirmed 72 h after streptozotocin injection by measurement of blood glucose levels using Contour® blood glucose diagnostic kit (Bayer HealthCare, Canada). Body weight and blood glucose levels were measured before and 3 days after streptozotocin injection, once a week for three weeks after diabetes induction. Only rats having blood glucose concentration consistently higher than 300 mg/dl were used for the present study.

Treatment Paradigms

To investigate whether RCT02 (all-D-TTNYT), a drug which acts directly on CCR5 and CCR3 chemokine receptors can reverse already established neuropathic hypersensitivity in diabetic rats, autoclaved water or RCT02 (0.004, 0.02, 0.1 or 0.5 mg/kg b.w.) was administered daily by oral gavage to rats who exhibited stable mechanical and cold allodynia. The treatment lasted for 8 days Note, n=5 for $H_2O$ and n=7 for RAP-103/each dose.

Assessment of Pain Sensitivity

Tactile allodynia Mechanical sensitivity was assessed using calibrated von Frey hairs (7). Animals were placed in Plexiglas boxes on an elevated metal mesh floor and allowed 60 min for habituation before testing. A series of von Frey filaments with logarithmically incrementing stiffness was applied perpendicular to the mid-plantar region of the hind paw. The 50% paw withdrawal threshold was determined using Dixon's up-down method. Withdrawal thresholds of both paws were averaged as one single value per animal. Assessment on the effects of RAP103 on mechanical and cold allodynia was performed between 2-4 hours following the drug administration. FIG. 1 shows the action of R103 to block mechanical pain, while FIG. 2 shows the action of R103 to block cold allodynia. FIGS. 3A-F shows the action of R103 to reduce CNS (dorsal spinal cord) chemokines and chemokine receptors predicted to stop or reduce drug-seeking behaviors or the behavioral effects of substance abuse. All data were presented as means±SEM. Statistical analysis was performed by two-way ANOVA followed by Bonferroni post-tests. The criterion for statistical significance was $P<0.05$.

Locomotor Experiments

Figure 1A:
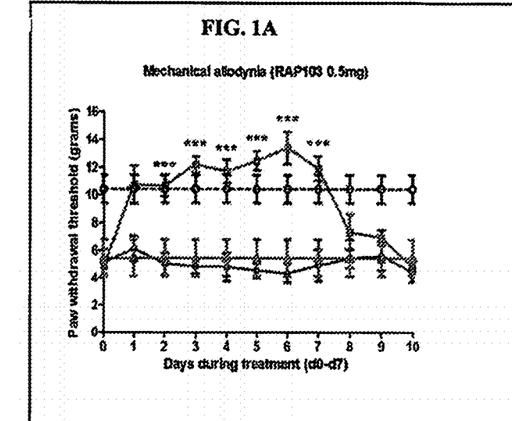
FIGS. 1A-D illustrate that RAP-103 reversed mechanical allodynia in streptozotocin (STZ) induced diabetic rats by blocking chemokine receptors CCR2 and CCR5. Nerve-injured rats treated with vehicle only (H2O) developed a bilateral hypersensitivity to mechanical stimuli. Oral administration of SEQ ID No.:1 (RAP-103) (A, B, C, D) to nerve-injured rats completely prevented the development of mechanical allodynia. (*) P<0.05, (**) P<0.01. Data are presented as mean±SEM; n=4 per group.
Figure 1B:
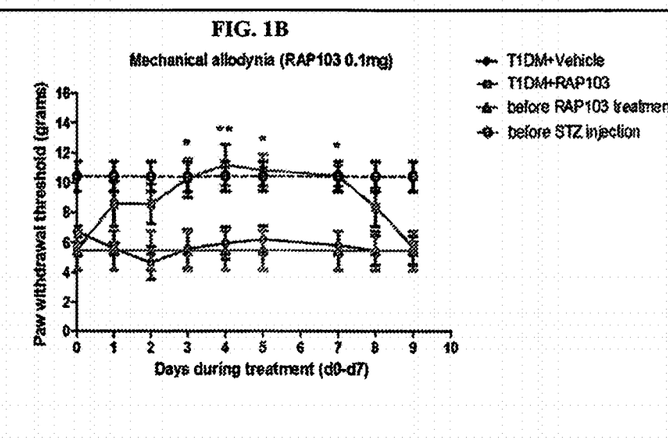
Figure 1C:
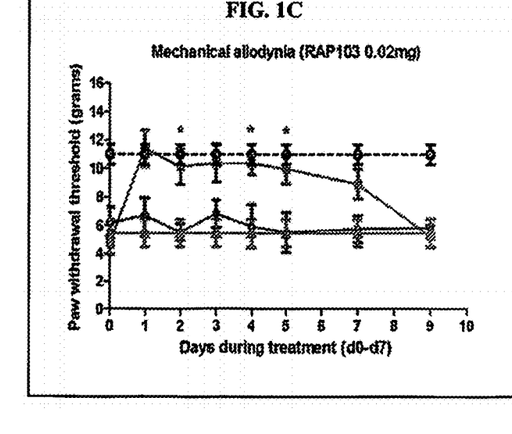
Figure 1D:
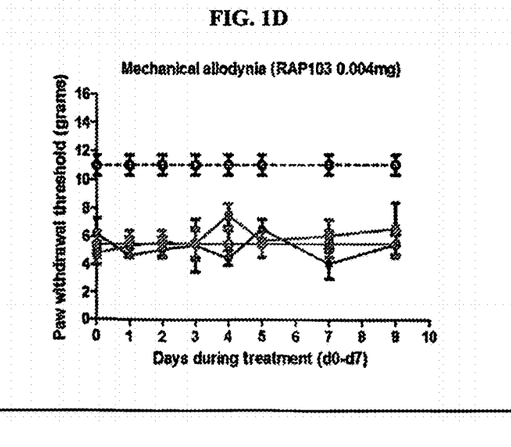
Figure 2A:
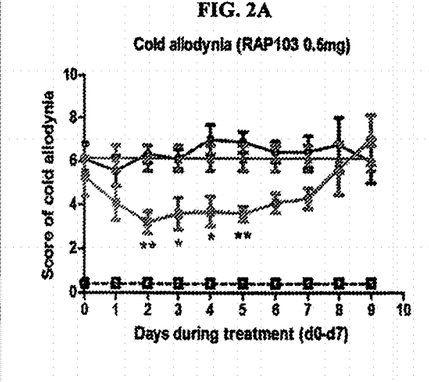
FIGS. 2A-D illustrate SEQ ID No.:1 (RAP103) reversed cold allodynia in STZ induced diabetic rats. Oral administration of RAP103 (A, B, C, D) to nerve-injured rats completely prevented the development of mechanical allodynia. (*) P<0.05, (**) P<0.01. Data are presented as mean±SEM; n=4 per group.
Figure 2B:
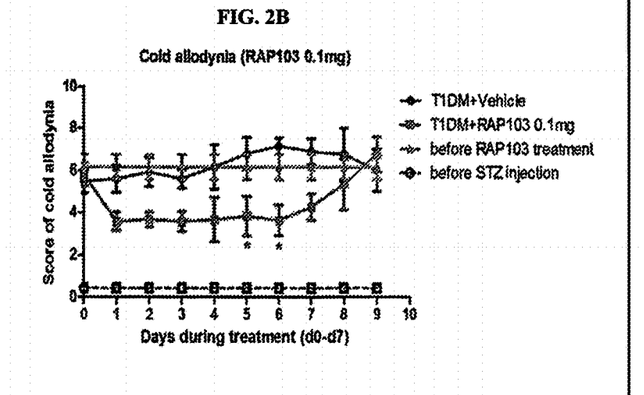
Figure 2C:
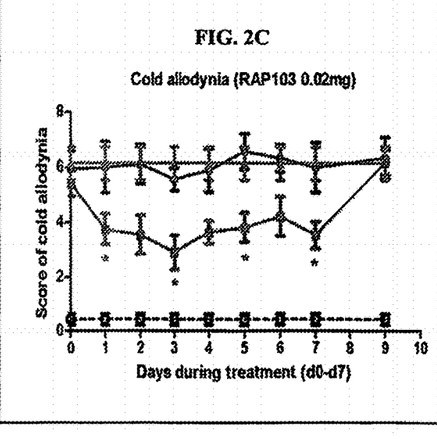
Figure 2D:
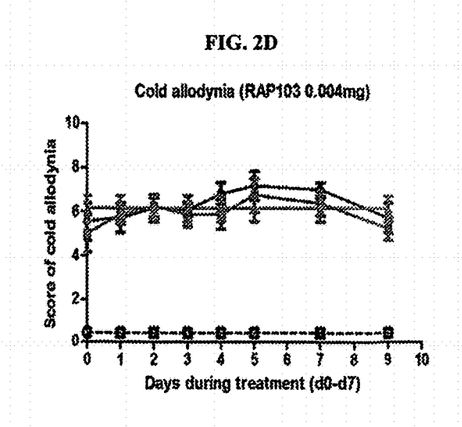
Figure 3A:
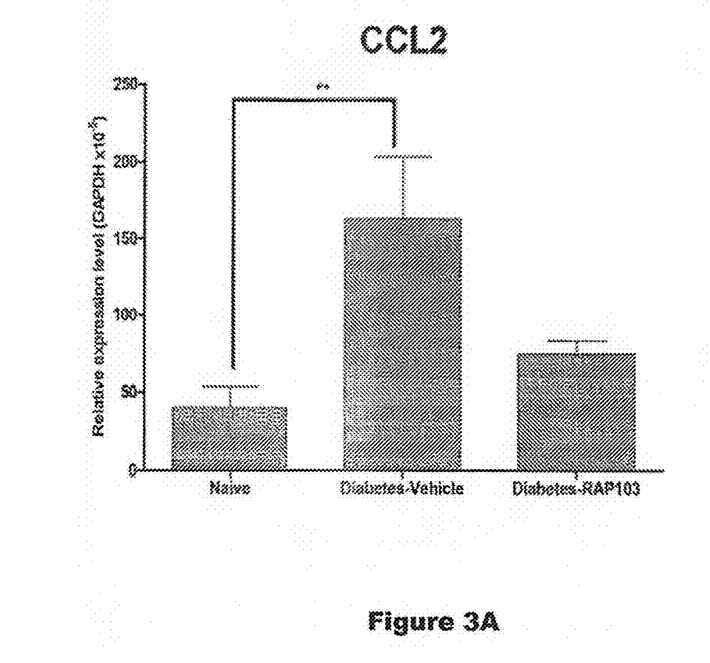
FIGS. 3A-F illustrate RAP103 (0.5 mg/kg, for 7 days, p.o.) significantly inhibited inflammation (CCL2, FIG. 3A; CCL3, FIG. 3B) in the sciatic nerves of STZ rats
Figure 3B:
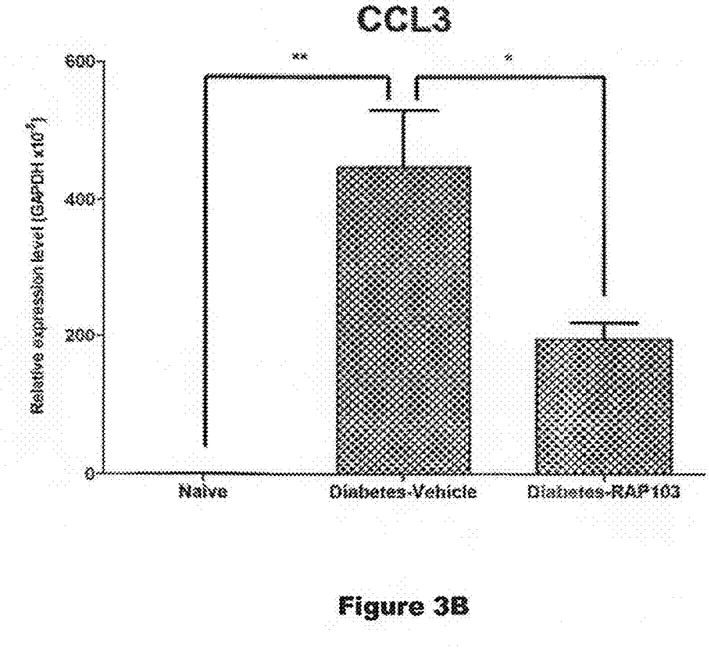
Figure 3C:
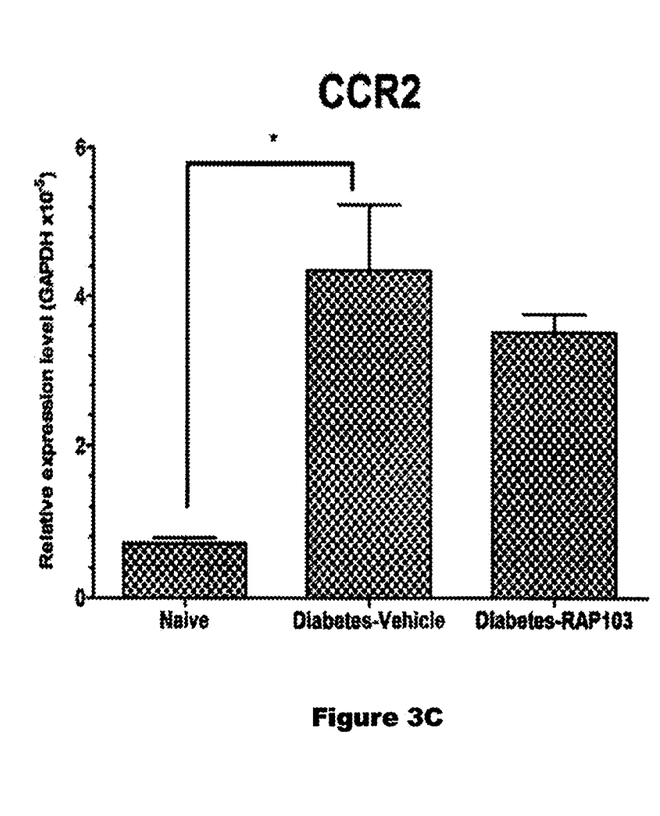
Figure 3D:
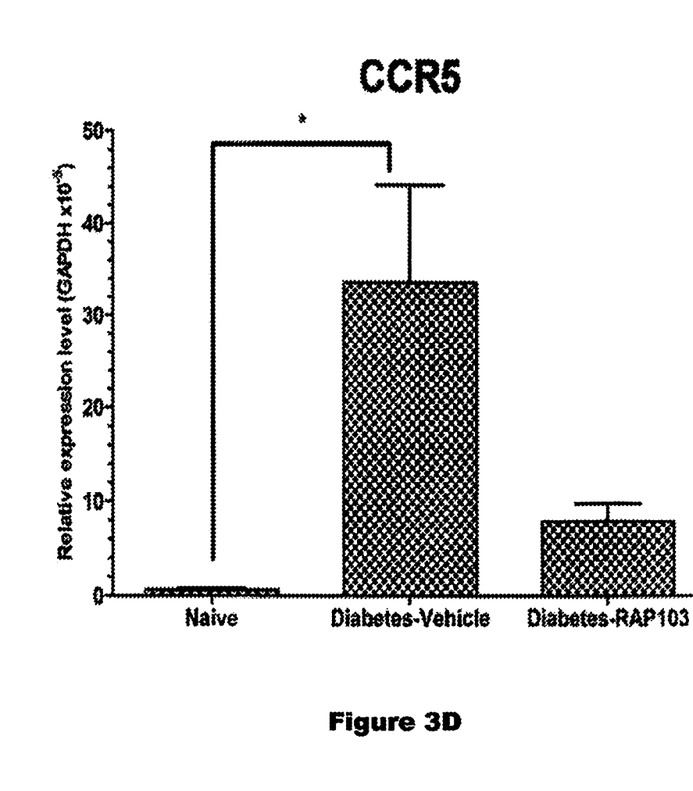
Figure 3E:
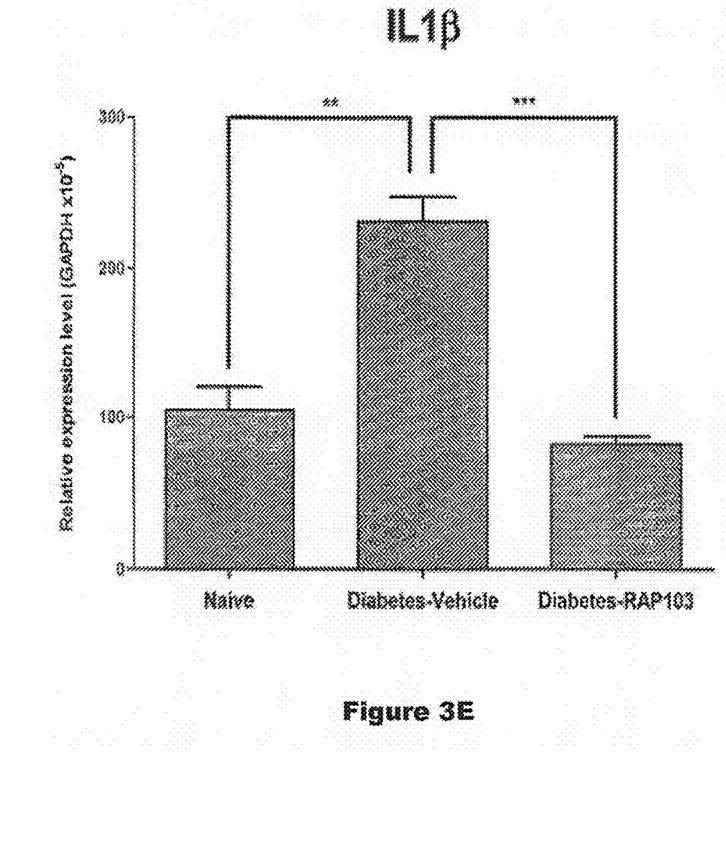
Figure 3F:
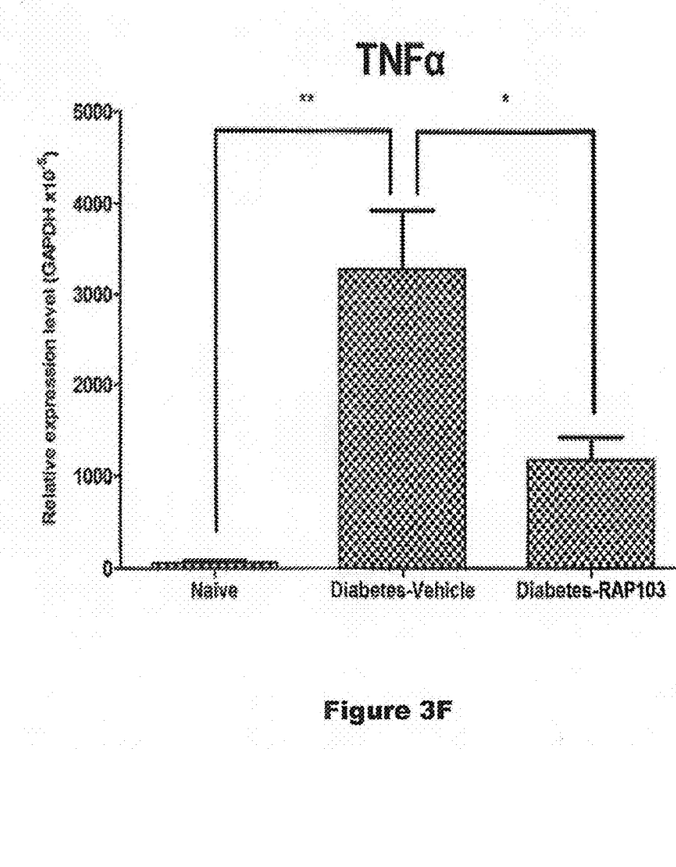
Figure 4:
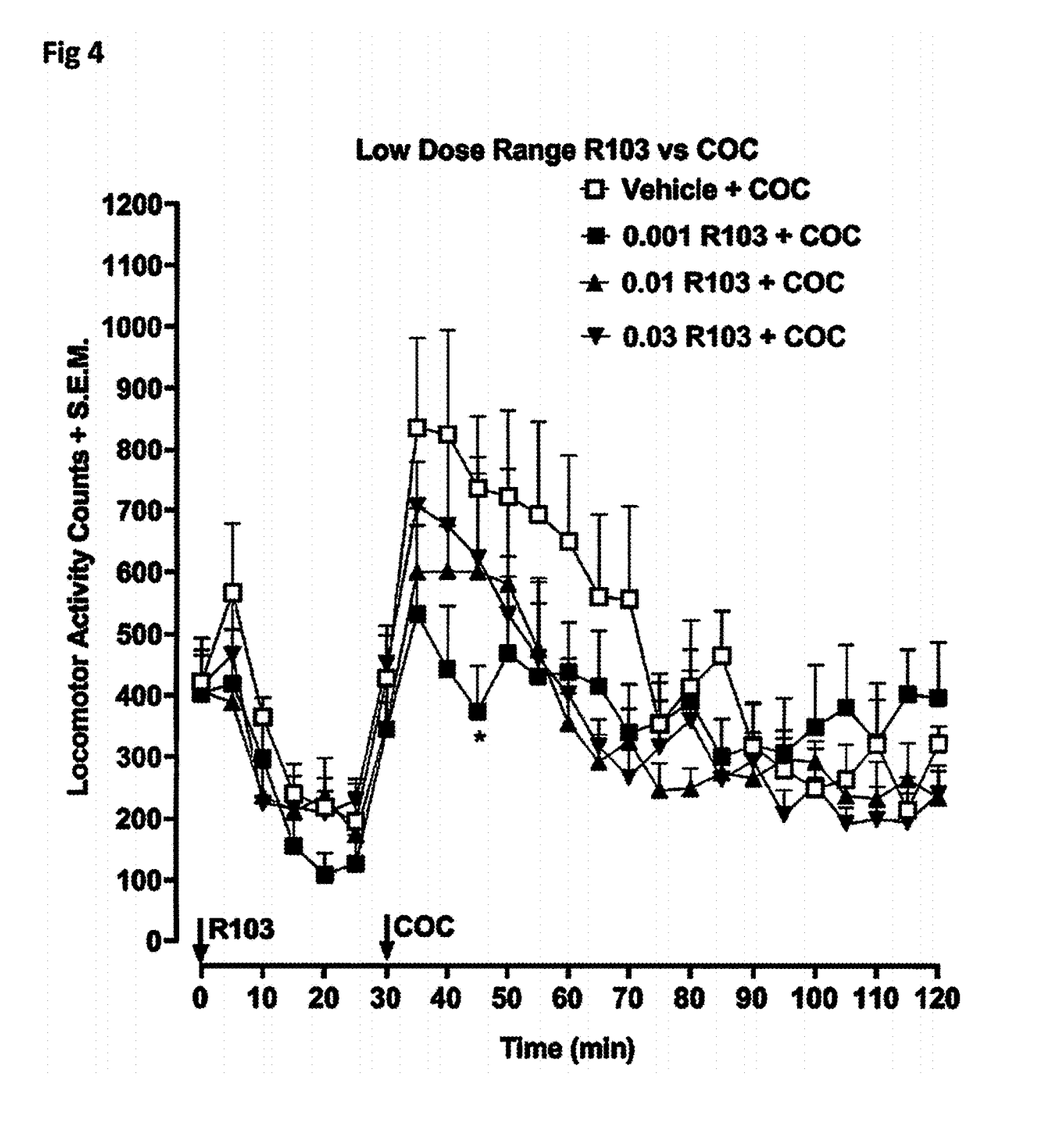
FIG. 4 illustrates RAP103 (0.001, 0.01, 0.03 mg/kg, p.o.) inhibited psychostimulant cocaine induced locomotor behavior. Time-course data showing effects of RAP-103 pretreatment on cocaine hyperlocomotion are presented as locomotor activity counts/5 min. N=7-8 rats/group. *p<0.05 compared to cocaine only. Data are presented as cumulative locomotor counts from 0-60 min following cocaine (C) or vehicle administration (VEH).

Locomotor activity (ambulation+stereotypy) induced by cocaine and the effect of RAP-103 was assessed using a Digiscan DMicro system. Following a 60-min habituation in activity chambers, rats were pretreated with RAP-103 (0.03, 0.01, 0.001 mgs/Kg) or vehicle 30 min before cocaine (10 mgs/Kg) or vehicle and activity was measured for 120 min. Differences between individual groups were determined with a Bonferroni post-hoc test. Statistical significance was set at $p<0.05$. We show that RAP-103 blocks the locomotor inducing effects of cocaine (FIG. 4).

Effects of R103 on MOR Withdrawal in Rats.

Figure 5:
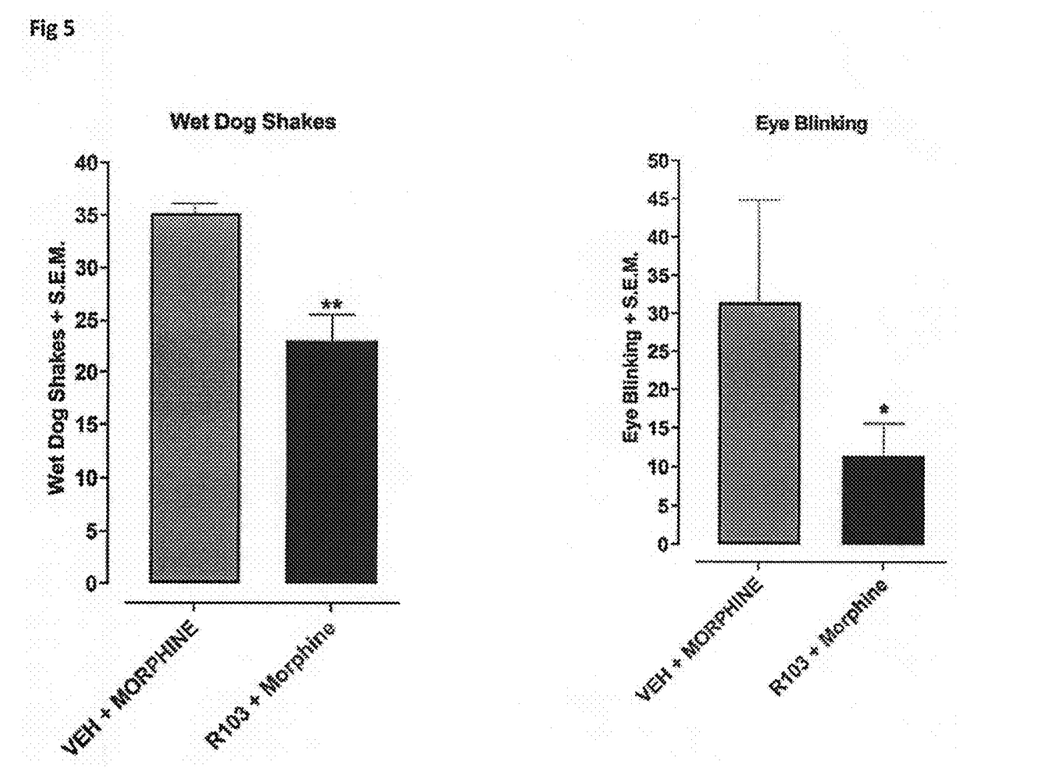
FIG. 5 illustrate RAP103 significantly inhibited naloxone precipitated withdrawal signs in rodents (wet dog shakes and eye blink).
Figure 6:
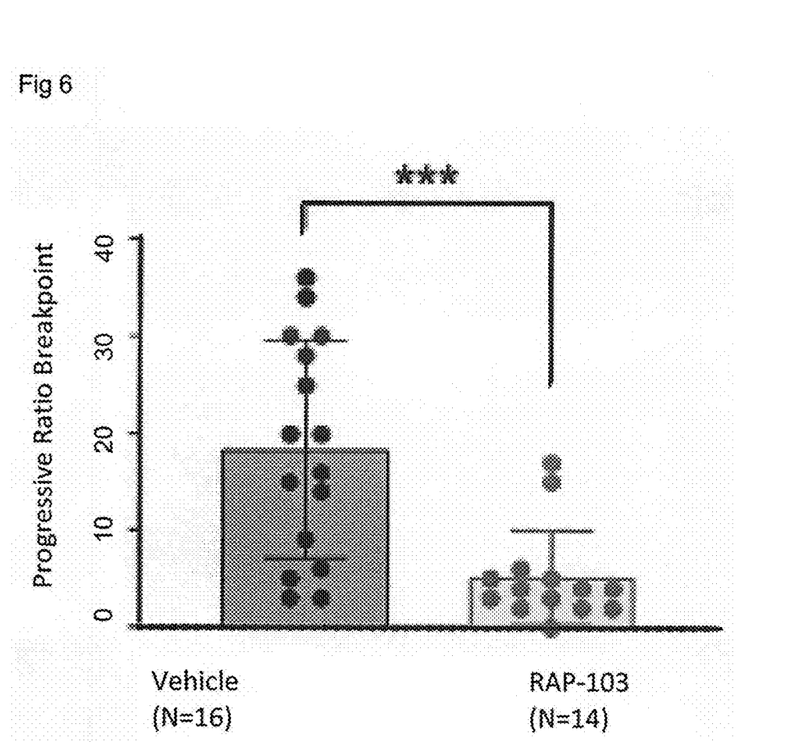
FIG. 6 illustrates RAP103 significantly inhibited opioid self-administration by lever press for drug infusions.

Opioid tolerance during chronic exposure requires increasing opioid doses to maintain analgesic efficacy. Physical dependence also develops during chronic opioid exposure and, upon discontinuation of opioid intake, presents as a withdrawal syndrome that triggers opioid relapse. We tested the effects of RAP-103 (0.5 mg/kg) on naloxone-precipitated withdrawal signs in MOR-dependent rats. To induce physical dependence we implanted opioid (heroine) containing pellets. On day 7 rats received naloxone (3 mg/kg, SC) with or without added RAP-103 and the withdrawal signs of wet dog shakes and eye blinking were quantified for 60 min. We show that RAP-103 blocks naloxone-precipitated withdrawal signs, and therefore is predicted protect to relapse to drug seeking behaviors, FIG. 5.

Effects of R103 on MOR Physical Dependence in Rats.

Rats were surgically prepared to have indwelling catheters prior to self-administration testing. To begin each session, house lights were turned on and two retractable levers extended into the chamber. Rats were trained on a Fixed Ratio schedule of one (FR) schedule to lever press for drug infusions during daily 2-h sessions during which a response on the active lever will result in a 3-s MOR infusion (0.25 mg/kg/inf) and simultaneous light cue+tone stimulus. Responses on the inactive lever will have no consequences but were recorded to monitor for nonspecific motor behaviors. A 20-s timeout period will follow each infusion to limit possibility of overdose. After stable responding under the FR-1 schedule (<10% changes in mean number of reinforcers earned for 3 consecutive days, 75% of total responses corresponding to active lever presses), rats will be switched to a Partial Ratio (Intermittent, PR) schedule for determination of stable break point, a measure of motivation to self-administer a drug. For PR studies, a fixed dose of MOR (0.25 mg/kg/inf) was used because this dose can yield higher break points indicative of high motivation to obtain drug. The dependent variable measured will be the number of infusions earned by the end of the session and defined as the breakpoint. Total cumulative responses made by the rat on the active lever during each session will also be recorded. Once rats reach criteria for stable PR responding, which is defined as 3 consecutive days of responding without upward or downward variance (<20% change from mean number of reinforcers earned for 3 consecutive days), R103 (0.02, 0.1, and 0.5 mg/kg) will be administered 15 min before daily SA sessions to assess effects on breaking point and to obtain dose-effect data for R103. A repeated-measures 2-way ANOVA (R103 treatment, sex) between-subjects design followed by a Bonferroni test was used. We show that progressive-ratio experiments revealed that the motivation to work for reinforcer, that is self-administer an opioid, was significantly reduced in RAP-103 treated rats, FIG. 5.

REFERENCES

1. Crews F T, Zou J, Qin L. Induction of innate immune genes in brain create the neurobiology of addiction. Brain, behavior, and immunity. 2011; 25 Suppl 1:S4-s12. Epub 2011/03/16. PubMed PMID: 21402143; PMCID: PMC3552373.
2. He J, Crews F T. Increased MCP-1 and microglia in various regions of the human alcoholic brain. Experimental neurology. 2008; 210(2):349-58. Epub 2008/01/15. PubMed PMID: 18190912; PMCID: PMC2346541.
3. Kim J, Connelly K L, Unterwald E M, Rawls S M. Chemokines and cocaine: CXCR4 receptor antagonist AMD3100 attenuates cocaine place preference and locomotor stimulation in rats. Brain, behavior, and immunity. 2017; 62:30-4. Epub 2016/08/31. PubMed PMID: 27575003; PMCID: PMC5326690.
4. Nayak S U, Cicalese S, Tallarida C, Oliver C F, Rawls S M. Chemokine CCR5 and cocaine interactions in the brain: Cocaine enhances mesolimbic CCR5 mRNA levels and produces place preference and locomotor activation that are reduced by a CCR5 antagonist. Brain, behavior, and immunity. 2020; 83:288-92. Epub 2019/09/27. PubMed PMID: 31557508; PMCID: PMC6906231.
5. Trocello J M, Rostene W, Melik-Parsadaniantz S, Godefroy D, Roze E, Kitabgi P, Kuziel W A, Chalon S, Caboche J, Apartis E. Implication of CCR2 chemokine receptor in cocaine-induced sensitization. J Mol Neurosci. 2011; 44(3):147-51. Epub 2011/03/23. PubMed PMID: 21424761.
6. Saika F, Matsuzaki S, Kobayashi D, Kiguchi N, Kishioka S. Chemokine CXCL1 is responsible for cocaine-induced reward in mice. Neuropsychopharmacology reports. 2018; 38(3):145-8. Epub 2018/09/04. PubMed PMID: 30175527.
7. Padi S, Shi X, Zhao Y, Ruff M, Baichoo N, Pert C, Zhang J. Attenuation of rodent neuropathic pain by an orally active peptide, RAP-103, which potently blocks CCR2- and CCR5-mediated monocyte chemotaxis and inflammation. Pain. 2012; 153(1):95-106. PubMed PMID: 22033364.

What is claimed is:

1. A method of treating a patient with a substance abuse disorder, wherein the substance is cocaine, the method comprising:
   administering to the patient a therapeutically effective dose of a pharmaceutical composition that comprises:
   (i) a chemokine receptor antagonist that comprises five contiguous amino acids having the general structure: A-B-C-D-E in which:
   A is Ser, Thr, Asn, Glu, or Ile,
   B is Ser, Thr, Asp, or Asn,
   C is Thr, Ser, Asn, Arg, or Trp,
   D is Tyr,
   E is Thr, Ser, Arg, or Gly, wherein all stereoisomeric amino acids in A-B-C-D-E are in the D configuration, wherein the chemokine receptor antagonist is at most eight (8) amino acid residues in length, and
   (ii) a pharmaceutically acceptable carrier,
   wherein the administering of the therapeutically effective dose results in a reduction of a symptom associated with the substance abuse disorder, as compared to the patient before the administering, thereby treating the substance abuse disorder.

2. The method of claim 1, wherein component E further comprises a modification that enhances tissue distribution, the modification being selected from the group consisting of: esterified, glycosylated, and amidated.

3. The method of claim 1, in which the composition is in the form of an oral pill comprising the chemokine receptor antagonist in an amount ranging from 0.5 mgs to 100 mgs.

4. The method of claim 1, wherein the chemokine receptor antagonist comprises the D-peptide Thr Asn Tyr Thr (SEQ ID NO:1).

5. The method of claim 1, wherein all stereoisomeric amino acids in the at most eight amino acids are in the D configuration and comprise a sequence selected from the group consisting of:

Thr Thr Asn Tyr Thr, (SEQ ID NO: 1)

Ser Ser Thr Tyr Arg, (SEQ ID NO: 2)

Ser Thr Asn Tyr Thr, (SEQ ID NO: 3)

Thr Thr Ser Tyr Thr, (SEQ ID NO: 8)

Asn Thr Ser Tyr Gly, (SEQ ID NO: 4)

Glu Thr Trp Tyr Ser, (SEQ ID NO: 9)

Asn Thr Ser Tyr Arg, (SEQ ID NO: 10)

Ile Asn Asn Tyr Thr, (SEQ ID NO: 7)

Ile Asp Asn Tyr Thr, (SEQ ID NO: 11)

Thr Asp Asn Tyr Thr, (SEQ ID NO: 12)

Thr Asp Ser Tyr Ser, (SEQ ID NO: 13)

Thr Asn Ser Tyr Arg, and (SEQ ID NO: 14)

Asn Thr Arg Tyr Arg. (SEQ ID NO: 15)

6. The method of claim 1, wherein said chemokine receptor antagonist is all-D peptide T (astttnyt).

7. The method of claim 1, wherein the symptom comprises a withdrawal symptom.

8. The method of claim 2, wherein the modification comprises amidation and wherein the chemokine receptor antagonist is all-D DAPTA.

* * * * *

SEQUENCE LISTING

<160> NUMBER OF SEQ ID NOS: 15

<210> SEQ ID NO 1
<211> LENGTH: 5
<212> TYPE: PRT
<213> ORGANISM: Human immunodeficiency virus

<400> SEQUENCE: 1

Thr Thr Asn Tyr Thr
1               5

<210> SEQ ID NO 2
<211> LENGTH: 5
<212> TYPE: PRT
<213> ORGANISM: Human immunodeficiency virus

<400> SEQUENCE: 2

Ser Ser Thr Tyr Arg
1               5

<210> SEQ ID NO 3
<211> LENGTH: 5

-continued

<210> SEQ ID NO 3
<211> LENGTH: 5 (implied)
<212> TYPE: PRT
<213> ORGANISM: Human immunodeficiency virus

<400> SEQUENCE: 3

Ser Thr Asn Tyr Thr
1               5

<210> SEQ ID NO 4
<211> LENGTH: 5
<212> TYPE: PRT
<213> ORGANISM: Human immunodeficiency virus

<400> SEQUENCE: 4

Asn Thr Ser Tyr Gly
1               5

<210> SEQ ID NO 5
<211> LENGTH: 7
<212> TYPE: PRT
<213> ORGANISM: Human immunodeficiency virus

<400> SEQUENCE: 5

Ala Ser Thr Thr Asn Tyr Thr
1               5

<210> SEQ ID NO 6
<211> LENGTH: 7
<212> TYPE: PRT
<213> ORGANISM: Human immunodeficiency virus

<400> SEQUENCE: 6

Ala Ser Thr Thr Asn Tyr Thr
1               5

<210> SEQ ID NO 7
<211> LENGTH: 5
<212> TYPE: PRT
<213> ORGANISM: Human immunodeficiency virus

<400> SEQUENCE: 7

Ile Asn Asn Tyr Thr
1               5

<210> SEQ ID NO 8
<211> LENGTH: 5
<212> TYPE: PRT
<213> ORGANISM: Human immunodeficiency virus

<400> SEQUENCE: 8

Thr Thr Ser Tyr Thr
1               5

<210> SEQ ID NO 9
<211> LENGTH: 5
<212> TYPE: PRT
<213> ORGANISM: Human immunodeficiency virus

<400> SEQUENCE: 9

Glu Thr Trp Tyr Ser
1               5

<210> SEQ ID NO 10
<211> LENGTH: 5
<212> TYPE: PRT
<213> ORGANISM: Human immunodeficiency virus

```
<400> SEQUENCE: 10

Asn Thr Ser Tyr Arg
1               5

<210> SEQ ID NO 11
<211> LENGTH: 5
<212> TYPE: PRT
<213> ORGANISM: Human immunodeficiency virus

<400> SEQUENCE: 11

Ile Asp Asn Tyr Thr
1               5

<210> SEQ ID NO 12
<211> LENGTH: 5
<212> TYPE: PRT
<213> ORGANISM: Human immunodeficiency virus

<400> SEQUENCE: 12

Thr Asp Asn Tyr Thr
1               5

<210> SEQ ID NO 13
<211> LENGTH: 5
<212> TYPE: PRT
<213> ORGANISM: Human immunodeficiency virus

<400> SEQUENCE: 13

Thr Asp Ser Tyr Ser
1               5

<210> SEQ ID NO 14
<211> LENGTH: 5
<212> TYPE: PRT
<213> ORGANISM: Human immunodeficiency virus

<400> SEQUENCE: 14

Thr Asn Ser Tyr Arg
1               5

<210> SEQ ID NO 15
<211> LENGTH: 5
<212> TYPE: PRT
<213> ORGANISM: Human immunodeficiency virus

<400> SEQUENCE: 15

Asn Thr Arg Tyr Arg
1               5
```